(12) United States Patent
Duefel et al.

(10) Patent No.: US 8,580,949 B2
(45) Date of Patent: Nov. 12, 2013

(54) ENZYMATIC SYNTHESIS OF CARBA-NAD

(75) Inventors: Hartmut Duefel, Schlehdorf (DE); Dieter Heindl, Paehl (DE); Carina Horn, Biblis (DE); Thomas Meier, Munich (DE); Rainer Schmuck, Benediktbeuern (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/358,146

(22) Filed: Jan. 25, 2012

(65) Prior Publication Data

US 2012/0130062 A1    May 24, 2012

Related U.S. Application Data

(63) Continuation of application No. PCT/EP2010/004523, filed on Jul. 23, 2010.

(30) Foreign Application Priority Data

Jul. 27, 2009    (EP) ..................... 09166457

(51) Int. Cl.
    *C07H 19/207*    (2006.01)
(52) U.S. Cl.
    CPC .................... *C07H 19/207* (2013.01)
    USPC ...................... 536/27.6; 536/27.81
(58) Field of Classification Search
    None
    See application file for complete search history.

(56) References Cited

U.S. PATENT DOCUMENTS

2008/0213809 A1    9/2008    Heindl et al.

OTHER PUBLICATIONS

U.S. Appl. No. 13/201,564, filed Aug. 2011, Horn et al.*
U.S. Appl. No. 13/400,209, filed Feb. 2012, Roedel et al.*
International Search Report issued Sep. 13, 2010 in PCT Application No. PCT/EP2010/004523, 2 pages.
Molkentin, Jeffery D. and Dorn, Gerald W. II, "Cytoplasmic Signaling Pathways That Regulate Cardiac Hypertrophy," Annual Review of Physiology, 2001, pp. 391-426, vol. 63.
Piano, Mariann R. et al., "Cellular Events Linked to Cardiac Remodeling in Heart Failure: Targets for Pharmacologic Intervention," Journal of Cardiovascular Nursing, 2000, pp. 1-23, vol. 14, No. 4.
Slama, James T. and Simmons, Anne M., "Synthesis and Properties of Photoaffinity Labels for the Pyridine Dinucleotide Binding Site of NAD Glycohydrolase," Biochemistry, 1991, pp. 2527-2534, vol. 30.
Hutchinson, Edward J. et al., "Synthesis of carbocyclic NAD+ containing a methylenebisphosphonate linkage for the investigation of ADP-ribosyl cyclase," Collection of Czechoslovak Chemical Communications, pp. 2765-2766, vol. 61.

* cited by examiner

*Primary Examiner* — Eric S Olson
(74) *Attorney, Agent, or Firm* — Faegre Baker Daniels LLP

(57) ABSTRACT

The disclosure concerns the enzymatic synthesis of stable analogues of nicotinamide adenine dinucleotide NAD/NADH and nicotinamide adenine dinucleotide phosphate NADP/NADPH, the so-called "carba-NADs", i.e. analogues of NAD/NADH or NADP/NADPH, respectively, comprising a carbacyclic sugar instead of ribose.

21 Claims, 2 Drawing Sheets

ENZYMATIC SYNTHESIS OF CARBA-NAD

PRIORITY CLAIM

This application is a continuation of International Application No. PCT/EP2010/004523, filed Jul. 23, 2010, which claims the benefit of European Patent Application No. 09166457.3, filed Jul. 27, 2009, the disclosures of which are hereby incorporated by reference in their entirety.

FIELD OF THE DISCLOSURE

The instant disclosure relates to the synthesis of nicotinamide adenine dinucleotide ("NAD/NADH") and nicotinamide adenine dinucleotide phosphate ("NADP/NADPH"), the "carba-NADs". More specifically, the instant disclosure relates to the enzymatic synthesis of carba-NADs, and stable analogues thereof, comprising a carbacyclic sugar in place of ribose.

BACKGROUND OF THE DISCLOSURE

Many measuring systems for biochemical analytics comprise components of clinical analytical methods. Such systems generally include the measurement of analytes, e.g., metabolites or substrates, for example, which may be determined directly or indirectly with the aid of an enzyme. For example, an analyte of interest may be converted into another compound with the aid of an enzyme-coenzyme complex and subsequently quantified via this enzymatic reaction. In such process, the analyte to be determined may be brought into contact with a suitable enzyme and a coenzyme, under appropriate reaction conditions, whereby the coenzyme changes, e.g., is oxidized or is reduced by the enzymatic reaction. Such changes may be detected electrochemically or photometrically either directly or by means of a mediator. Further, a calibration curve may be constructed to provide a direct correlation between the measured value (of the detected change) and the change detected for known concentrations of the analyte of interest, thereby facilitating determination of the analyte's concentration.

Coenzymes, in general, comprise molecules which may be covalently or non-covalently bound to an enzyme and that themselves may be changed by the conversion of the analyte. By way of example, coenzymes include nicotinamide adenine dinucleotide ("NAD") and nicotinamide adenine dinucleotide phosphate ("NADP"), from which NADH and NADPH, respectively, are formed by an enzyme catalyzed reduction.

As described in US 2008/0213809, at least some of the disadvantages of conventional measuring systems, for example limited shelf-life and special storage condition requirements (such as cooling or dry storage) required in order to achieve improved shelf-life, may be abviated by using the stable NAD/NADH and NADP/NADPH derivatives disclosed therein. These NAD(P)H analogues may aid in reducing the occurrence of erroneous results resulting from the inadvertent use of degraded co-factors in critical assays. The use of NAD/NADH and NADP/NADPH derivatives that exhibit increased stability can be of utility especially when critical tests which are carried out by end-users such as patients performing glucose self-monitoring.

As described in US 2008/0213809 the chemical synthesis of carba-NAD is extremely challenging, involving a process that includes at least 8 steps. These processes generally provide relatively low yields, and are quite expensive. A representative chemical route for the synthesis of carba-NAD is depicted in FIG. 1. Accordingly, there is a need for alternative methods of synthesizing carba-NAD. Ideally these alternative methods should be less cumbersome, provide larger yields, and be more cost-effective than are the organic chemistry based methods currently in use. Some aspects of the instant disclosure seek to address this need.

SUMMARY OF THE DISCLOSURE

The present disclosure includes unexpected results illustrating that it is possible to utilize enzymes, instead of conventional synthetic organic chemistry, in order to synthesize carba-NADs in a cost-effective and convenient manner.

The present disclosure provides methods for enzymatically synthesizing carba-NADs, or analogues thereof. These methods may include a step of phosphorylating a 3-Carbamoyl-1-(2,3-dihydroxy-4-hydroxymethyl-cyclopentyl)-pyridinium-methansulfonate, or an analogue thereto, with the aid of an nicotinamide-ribosyl kinase ("NRK") enzyme. These methods also include a step of adenylating the phosphorylated product (of the phosphorylating step) with adenosine, or a structurally related compound, with the aid of a nicotinamide nucleotide adenylyltransferase ("NMN-AT") enzyme.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

Figure 1:
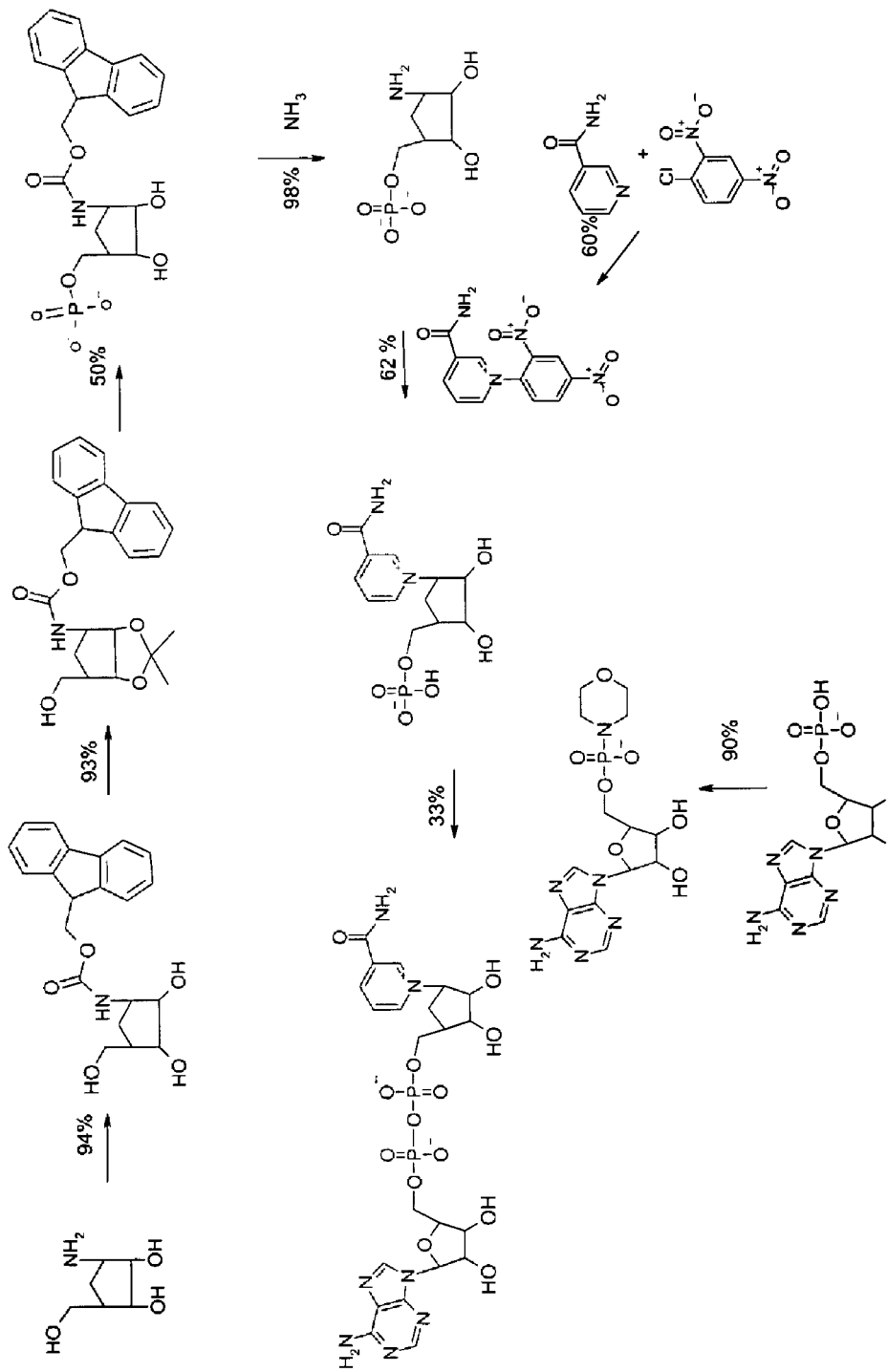
FIG. 1 (Prior Art) is a schematic illustration of the standard route used to chemically synthesize carba-NAD (cNAD). As indicated by the percentages given, the total yield according to this procedure is rather low.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

Figure 2:
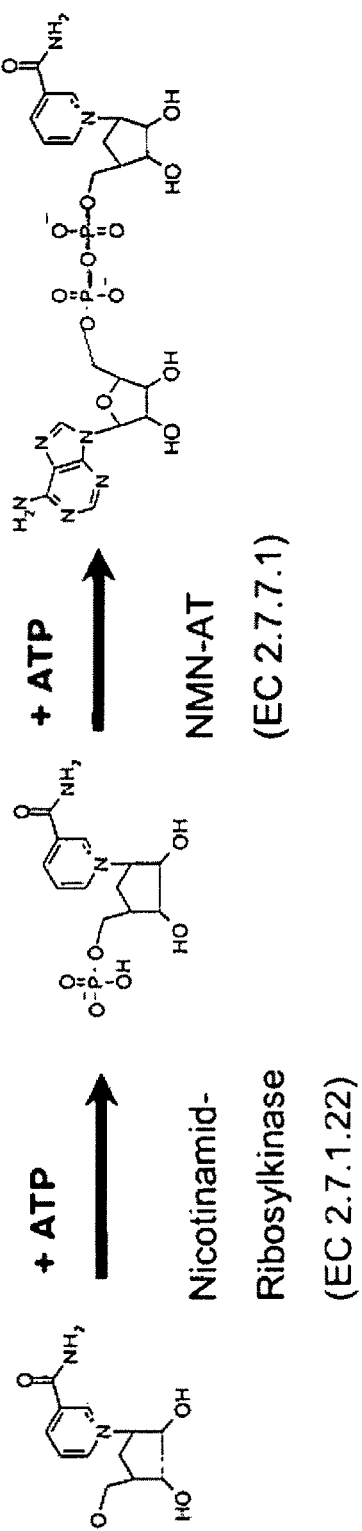
FIG. 2 is a schematic illustration of two enzymatic steps used in the synthesis of carba-NAD according to the present disclosure.

Referring now to FIG. 2, embodiments of the present disclosure relate to methods for synthesizing carba-NAD, or an analogue thereof, comprising the steps of:

a) phosphorylating a compound comprising Formula I with the aid of a NRK enzyme, Formula I

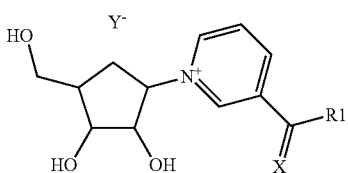

wherein R1 is OH, NH$_2$, O-methyl or N-dimethyl, methyl, Y$^-$ is a counter ion and X is O or S; and b) adenylating the phosphorylated product of step (a) with a compound of Formula II by aid of an NMN-AT enzyme, Formula II

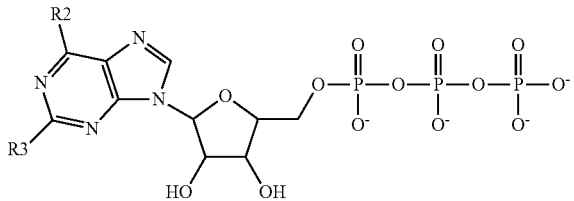

wherein R2 is NH$_2$, OH, or NHalkyl,
wherein R3 is H, OH, NH$_2$;
thereby obtaining carba-NAD, or an analogue thereof, comprising Formula III, Formula III

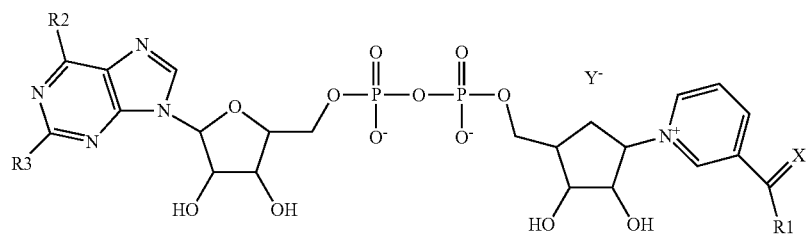

wherein, R1, R2, R3, Y$^-$ and X are defined as above (with respect to Formulas I and II).

As used herein, unless otherwise noted, the term "carba-" indicates the presence of a 2,3-dihydroxycyclopentane instead of a ribosyl sugar residue. For example, a carba-analogue of oxidized NAD ("NAD") comprises a compound otherwise identical to NAD' except that a 2,3-dihydroxycyclopentane ring replaces the D-ribonucleotide ring of the nicotinamide riboside moiety.

Enzymes are bio-catalysts that catalyze specific reactions enabling these reactions to occur at (or near) physiological conditions. Many of the reactions catalyzed by enzymes would only occur under harsher and therefore more undesirable conditions were it not for the aid of the enzyme. In order to effectively catalyze specific reactions, most enzymes are evolved to be highly specific for the substrates that they act upon and for the reactions that they catalyze. Accordingly, as disclosed herein it was surprising to find that NRK enzymes can accept as substrates the pyridinium compounds of Formula I comprising a 2,3,dihydroxycyclopentane ring, instead of a ribosyl group as is found in its naturally occurring substrate, and that NRK enzymes are also capable of phosphorylating these compounds.

According to international enzyme nomenclature, NRK enzymes are grouped into class EC 2.7.1.22 (ATP:N-ribosylnicotinamide 5'-phosphotransferases). In some embodiments of the present disclosure, an enzyme chosen from class EC 2.7.1.22 is used in the methods disclosed herein to catalyze the phosphorylation of a compound with the structure provided in Formula I.

As used herein the term NRK refers to enzymes that catalyze the phosphorylation of the ribosyl residue, these enzyme are widely distributed in nature and reported on in the literature. The various names for these enzymes include, for example, ribosylnicotinamide kinase and ribosylnicotinamide kinase (phosphotransferase). In nature they generally catalyze the transfer of a phosphate moiety from ATP to N-ribosylnicotinamide to form ADP and nicotinamide ribonucleotide. Exemplary NRKs that can be used to practice some embodiments of the instant disclosure include those found in *Saccharomyces cerevisiae* and *Pseudomonas aeruginosa*. Additional exemplary NRKs that can be used to practice the disclosure include those found in *Streptococcus sanguinius* and *Homo sapiens*. In some embodiments of the present disclosure, NRK1 from *Homo sapiens* may be used in order to perform phosphorylating steps according to the present disclosure.

Referring now to Formula I, not only carba-nicotinamide (wherein R1 is NH$_2$), but also other compounds such as the carba-nicotinamide analogues, including those compounds summarized by the alternatives given for R1 represent appropriate substrates for NRK enzymes. Having knowledge of the present disclosure a skilled artisan will understand how to investigate the compounds of Formula I, as well as related compounds, for their ability to be effectively phosphorylated by one or more NRK enzymes. In some specific embodiments of the present disclosure, the pyridinium compounds disclosed in Formula I are used for enzymatic phosphorylation Analogues to nicotinamide as defined in Formula I, include compounds wherein R1 is not NH$_2$. As disclosed herein, R1 of Formula I may be selected from the group comprising OH, NH$_2$ and O-methyl. In some embodiments, R1 is OH and in still other embodiments R1 is NH$_2$. Alkyl groups represented by R1 or R2 may comprise C1 to C6 linear or branched alkyls.

Additionally, as disclosed herein, the residue X in Formula I may comprise O or S. In still other embodiments, X in Formula I comprises O.

Further, as disclosed herein, the counter ion Y$^-$ may be selected from the group comprising methylsulfonate, Cl$^-$, PF$_6^-$, BF$_4^-$, and ClO$_4^-$. According to some embodiments of the present disclosure, the counter ion in Formula 1 comprises BF$_4^-$. According to other embodiments of the present disclosure, the counter ion may comprise methylsulfonate.

Surprisingly, the enzyme NMN-AT can utilize the phosphorylated carba-nicotinamide, obtained as described above, as acceptor molecules and is able to adenylate these compounds. In the second step of the enzymatic synthesis of carba-NAD (or an analogue thereof) NMN-AT is used to transfer an adenyl residue or an analogue thereof to the phosphorylated carba-nicotinamide (or analogue thereof), thereby forming carba-NAD or an analogue thereof.

NMN-ATs, according to international enzyme nomenclature, are grouped into class EC 2.7.7.1 (ATP:NMN-AT). According to an embodiment of the present disclosure, an enzyme chosen from class EC 2.7.7.1 is used to adenylate a phosphorylated compound of Formula I with a compound according to Formula II. Exemplary NMN-ATs include NMN-ATs from *Bacillus subtilis*, *Escherichia coli*, *Methanococcus janashii*, *Sulfolobus solfataricus*, *Saccharomyces cerevisiae* and *Homo sapiens*. In some embodiments of the instant disclosure, NMN-AT from *Homo sapiens* (and expressed, for example, in *E. coli* or *B. subtilis*) may be used to perform the adenylation enzymatic reaction. For the sake of convenience, unless expressly stated otherwise, as used herein, the terms "adenylate", "adenylated" and "adenylation" are used interchangeably to include the process by which a phosphorylated compound of Formula I is used as a substrate for NMN-AT.

Additionally, the instant disclosure also includes the unexpected result that both the phosphorylation and the adenylation steps, in the enzymatic synthesis of carba NAD (or an analogue thereof), can be performed in a single reaction mixture. Accordingly, embodiments of the present disclosure include methods for enzymatically synthesizing carba-NAD or an analogue thereof comprising the steps of phosphorylating a 3-Carbamoyl-1-(2,3-dihydroxy-4-hydroxymethyl-cyclopentyl)-pyridinium-methansulfonate (or an analogue thereof) with the aid of an NRK enzyme and adenylating the phosphorylated product with adenosine, or a structurally related compound, with the aid of an NMN-AT enzyme. In some embodiments, both enzymatic reactions are performed in one reaction mixture.

The instant disclosure includes the surprising result that, based on the methods disclosed herein, the biologically relevant enantiomer of cNAD which is based on the 1R,2S,3R,4R enantiomer of Carbamoyl-1-(2,3-dihydroxy-4-hydroxymethyl-cyclopentyl)-pyridinium can be obtained in pure form and at high yield. As disclosed herein, an embodiment of the methods disclosed herein may be used to synthesize cNAD comprising the 1R,2S,3R,4R enantiomer of Carbamoyl-1-(2,3-dihydroxy-4-hydroxymethyl-cyclopentyl)-pyridinium.

Referring now to Formula II, not only adenosine-tri-phosphate, but other structurally related compounds like the ones characterized by the definitions given for R2 and R3 in Formula II having various combinations of R2 and R3, respectively, are substrates for certain NMN-AT enzymes. A skilled artisan with knowledge of the instant disclosure will understand how to investigate the compounds of Formula II, as well as structurally related compounds, for their ability to be effectively adenylated by one or more NMN-AT enzymes.

Compounds that are structurally related to adenosine include compounds as defined in Formula II, wherein R2 is not NH$_2$ and wherein R3 is not H, respectively. According to the present disclosure, the purine compounds as defined by the groups given for R2 and R3 in Formula II may be used for the enzymatic adenylation of a phosphorylated carba-nicotinamide or an analogue thereof.

Further embodiments of the present disclosure relate to the use of compounds that are related to a compound of Formula II and selected from the group comprising the triphosphates of Nebularine, Formycin, aristeromycin, 7 deaza-adenosin, 7 deaza-guanosin, 7 deaza-inosin, 7 deaza-xanthosin, 7 deaza 2,6-diamino purine, 7 deaza 8 aza-adenosin, 7 deaza 8 aza-guanosin, 7 deaza 8 aza-inosin, 7 deaza 8 aza-xanthosin, 7 deaza 8 aza 2,6-diamino purine, 8 aza-adenosin, 8 aza-guanosin, 8 aza-inosin and 8 aza-xanthosin and 8 aza 2,6-diamino purine. According to the instant disclosure, these compounds may also be used to produce a corresponding dinucleotide comprising a carba analogue of nicotinamide in the methods disclosed herein.

According to some embodiments of the present disclosure, R2 of Formula II may be selected from the group comprising NH$_2$ or OH. In some embodiments R2 is OH and in yet another embodiment R2 is NH$_2$.

Additionally, according to some embodiments of the present disclosure R3 of Formula II is selected from the group comprising H or OH.

In one exemplary embodiment of the instant disclosure, the methods disclosed herein may be practiced with the compounds given in Formulas I, II and III, wherein R1 is NH$_2$, R2 is NH$_2$, R3 is H, and X is O.

It should be understood that carba-NAD and/or its analogues, respectively, may not react in exactly the same way (or provide the same results) with the various specific and different enzymes which utilize NAD as a co-enzyme or a co-factor. Thus, a skilled artisan may choose the most appropriate and desired analogue out of the options presented herein.

The following Examples and Figures are provided to aid in understanding the present disclosure and for the purpose of demonstrating some of the various embodiments of the instant disclosure. These examples are not intended to, and should not be understood as, limiting the scope or spirit of the instant disclosure in any way. It should further be understood that modifications can be made in the procedures set forth without departing from the spirit of the instant disclosure.

EXAMPLES

Example 1

Synthesis of 5-Dimethylamino-4-methoxycarbonyl-penta-2,4-dienylidene-dimethyl-ammoniumtetrafluoroborate Example 1.1

Synthesis of Methyl-(2E)-3-(3-dimethylamino)prop-2-enoate

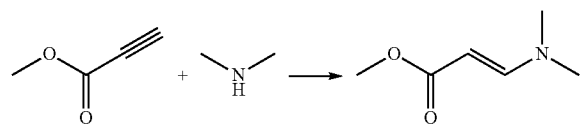

A 2 M solution of N,N-dimethylamine (392 ml, 0.783 mol) in tetrahydrofuran ("THF") solvent was added to a solution of methylpropiolate (68.0 ml, 0.764 mol) in 700 ml of dry THF within 1 h at room temperature. After removing the solvent, the resulting residue was dried for 1 h (37° C., 10-20 mbar) with an evaporator resulting in a pale yellow solid. The solid was crushed and washed with n-hexane to yield 93.0 g (94%)

methyl-(2E)-3-(3-dimethylamino)prop-2-enoate that, according to analysis with TLC and 1H NMR, was pure.

Example 1.2

Synthesis of Pyridiniumtetrafluoroborate

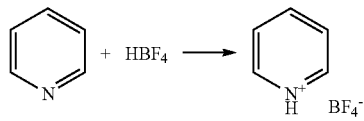

Tetrafluoroboric acid (250 ml, 2.00 mol) was added to cool (0° C.) pyridine (157.7 ml, 1.95 mol) within 25 mins. resulting in a colorless precipitate. After the acid was completely added, the mixture was further stirred for 30 mins. and held at the same temperature. Thereafter, the reaction mixture was filtered. The residue was washed twice with cold ethanol and dried for 12 hrs at high vacuum to yield 201.9 g (60%) of pyridiniumtetrafluoroborate in the form of colorless crystals.

Example 1.3

Synthesis of 5-Dimethylamino-4-methoxycarbonyl-penta-2,4-dienylidene-dimethyl-ammoniumtetrafluoroborate

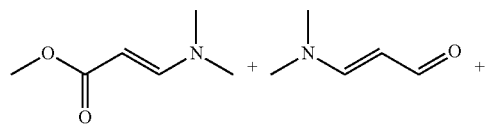

Pyridiniumtetrafluoroborate (283.7 g, 1.70 mol) was added to a solution of methyl-(2E)-3-(3-dimethylamino)prop-2-enoate in 442.5 ml acetic anhydride/acetic acid (2:1). The resulting suspension was cooled to 0° C. and 3-dimethylaminoacroleine (169.9 ml, 1.70 mol) was added slowly over the course of 3 hrs. under vigorous stirring and cooling with an ice bath, a yellow-brown precipitate formed. After further stirring for 2 hrs. at room temperature the reaction mixture was filtered. The remaining solid was washed with diethyl-ether several times and dried under reduced pressure. Re crystallization from i-propanol/ethanol (2:1) gave 326.7 g (65%) of the pentamethinium salt as yellow crystals.

Example 2

Synthesis of 2,3-Dihydroxy-4-hydroxymethyl-1-aminocyclopentan

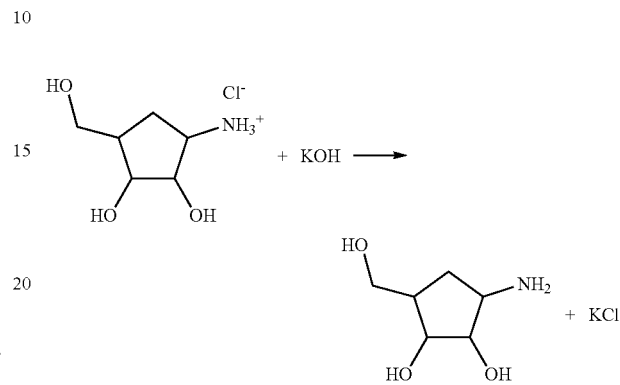

A 1M solution of KOH in EtOH (54.5 ml, 54.5 mmol) was added to a cooled (0° C.) solution of the hydrochloride (10.0 g, 54.5 mmol) dissolved in 540 ml EtOH. After 15 mins. of stirring at room temperature, the resulting colorless precipitate was removed by filtration. The filtrate was concentrated under reduced pressure. The remaining oil was dried with an evaporator (1 h, 40° C.) yielding 9.01 g (112%) of amino carbaribose as pale yellow oil. As described herein, the product obtained is used for the following steps without further purification.

According to the instant disclosure, this procedure may be used for synthesis of (1R,2S,3R,4R)-2,3-Dihydroxy-4-hydroxymethyl-1 aminocyclopentan and the enantiomer thereof.

Example 3

Synthesis of 1-(2,3-Dihydroxy-4-hydroxymethyl-cyclopentyl)-3-methoxycarbonyl-pyridinium-methansulfonate

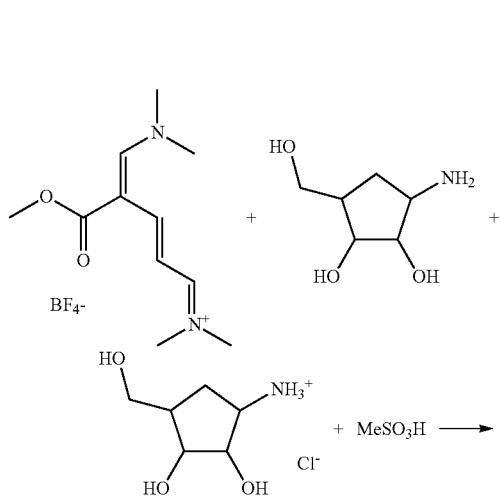

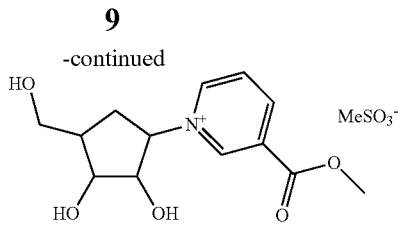

Vinamidinium salt (298.1 g, 1.00 mol) was dissolved in 1500 ml dimethylformamide ("DMF") and 1 equivalent of methanesulfonic acid (65.02 ml, 1.00 mol) was added. This mixture was dropped continuously and very slowly (within 5 h) to a refluxing solution (90° C.) of 3-Amino-5-hydroxymethyl-cyclopentane-1,2-diol (165.3 g, 0.90 mol) and 3-Amino-5-hydroxymethyl-cyclopentane-1,2-diol (25.8 g, 0.15 mol) in 1250 ml MeOH. After the complete addition of the vinamidinium salt solution, the reaction mixture was cooled to room temperature and 0.15 equivalents methanesulfonic acid were added. The mixture was stirred for 12 h at the same temperature. After removing the solvent under reduced pressure, a red-brown oil was obtained which was further dried for 3 hrs. (45° C., 4 mbar). Yield: 693.0 g (191%, containing salts and a larger amount of solvent).

According to the instant disclosure, this procedure may be used for the synthesis of 3-methoxycarbonyl-1-((1R,2S,3R,4R)-2,3-dihydroxy-4-hydroxymethyl-cyclopentyl)-pyridinium salt and the enantiomer thereof.

Example 4

3-C Carbamoyl-1-(2,3-dihydroxy-4-hydroxymethyl-cyclopentyl)-pyridinium-methansulfonate Crude 1-(2,3-Dihydroxy-4-hydroxymethyl-cyclopentyl)-3-methoxycarbonyl-pyridinium-methansulfonate material, obtained according to Example 3, was rapidly converted into the corresponding amide without further purification.

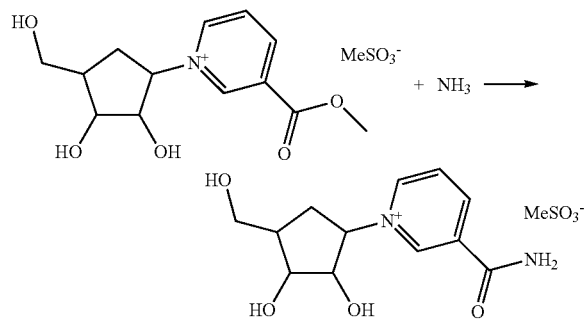

Crude 1-(2,3-Dihydroxy-4-hydroxymethyl-cyclopentyl)-3-methoxycarbonyl-pyridinium-methansulfonate (118.3 g, 173.7 mmol) was dissolved in 100.0 ml methanol. After the addition of methanolic ammonia (7M, 350.0 ml, 2.45 mol) the reaction mixture was stirred for 2.5 hrs. After removing the solvent under reduced pressure, a red-brown oil was obtained that was further dried for 3 hrs. (40° C., 10 mbar). This crude product may be pre-purified with activated charcoal and may be used directly for the chemical synthesis of cNAD (WO2007/012494) or in the enzymatic synthesis of cNAD as described herein.

Other compounds appropriate for use with the methods disclosed herein, see for example, the compounds defined in Formula I, can be synthesized in a manner analogous to the procedures given in Examples 1 thru 4 disclosed herein.

As disclosed herein, this procedure can be used for synthesis of 3-Carbamoyl-1-((1R,2S,3R,4R)-2,3-dihydroxy-4-hydroxymethyl-cyclopentyl)-pyridinium salt and the enantiomer thereof.

Example 5

Enzymatic Phosphorylation of Several Compounds According to Formula I with Nicotinamide-Ribosylkinase

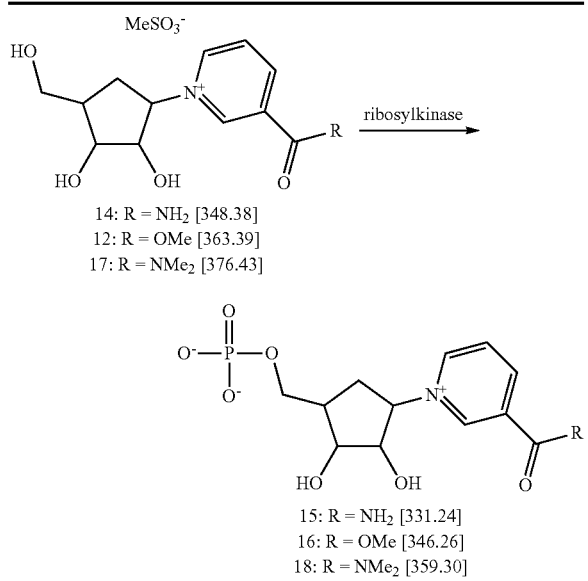

| Reagents | Amount |
|---|---|
| Pure (1R, 2S, 3R, 4R) enantiomers of 12, 14, 17, respectively, 100 mg/ml: | 100 μl |
| TRIS × HCl buffer pH 7.5, 15 mM MgCl$_2$: | 960 μl |
| ATP solution 100 mM/l: | 40 μl |
| creatine phosphate: | 14.5 mg |
| creatine kinase: | 0.1 mg |
| nicotinamide-ribosylkinase, 0.7 U/ml | 230 μl |
| (Recombinant NRK1 (ribosyl kinase) from *Homo sapiens* (SwissProt ID: Q9NWW6) or NRK (nadR) from *S. sanguinis* (SwissProt ID: A3CQV5), expressed heterologously in *E. coli*). | |

General Working Procedure:

Creatine phosphate (14.5 mg) and creatine kinase (0.1 mg) were dissolved in a mixture of TRIS buffer (pH 7.5, 15 mM MgCl$_2$, 960 μl) and ATP (100 mM/l in H$_2$O, 40 μl). A solution of the riboside (compound 14, or analogue thereof, as given above) (100 mg/ml in H$_2$O, 100 μl) was added, followed by the addition of ribosyl kinase (0.7 U/ml, 230 μl). The reaction mixture was incubated for 16 hrs. at 37° C. Next, the reaction mixture was warmed up to 80° C., filtered and analyzed by high performance liquid chromatography ("HPLC").

In all three cases (with compounds 14, 12 or 17, respectively) the complete consumption of the riboside and the formation of a new compound (corresponding to the phosphorylated product given as compounds 15, 16 or 18, respectively, above) was detected by HPLC.

Correct masses of the desired phosphorylated products were found via liquid chromatography—mass spectrometry ("LC/MS"): (MS: ESI: M$^-$=330.75 (compound 15), 345.74 (compound 16), 358.79 (compound 18)).

Compound 15 was purified by using chromatography on a cation exchange resin (Dowex) and elution with water.

Example 6

Enzymatic Conversion of Carba-Nicotimamide and Analogues Thereof, with NMN-AT

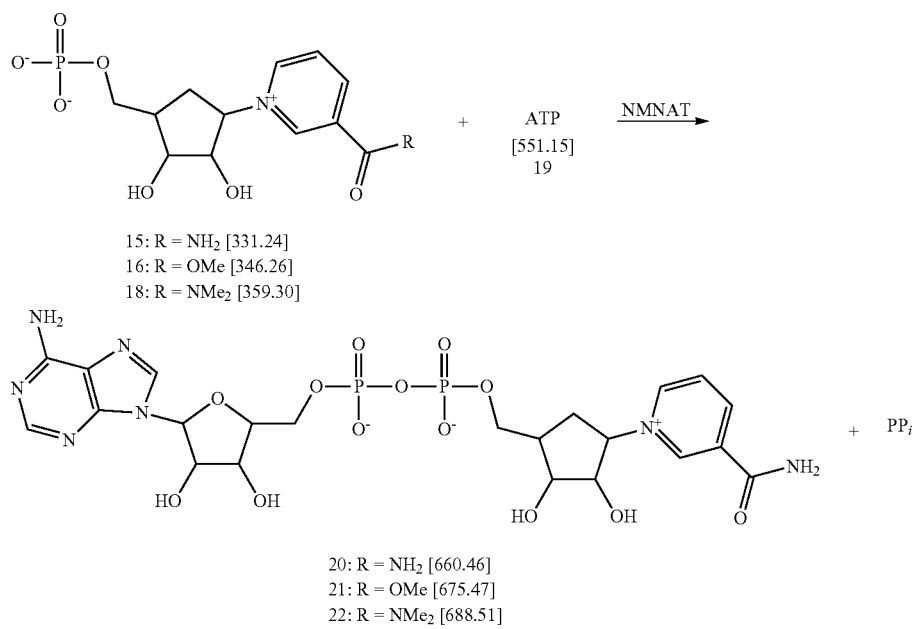

15: R = NH$_2$ [331.24]
16: R = OMe [346.26]
18: R = NMe$_2$ [359.30]

20: R = NH$_2$ [660.46]
21: R = OMe [675.47]
22: R = NMe$_2$ [688.51]

According to the instant disclosure, the following may be utilized in an enzymatic conversion of carba-nicotimamide (and analogues thereof), with NMN-AT. According to some embodiments of the instant disclosure, the enzymatic conversion of carba-nicotimamide (and analogues thereof) may include: compounds 15, 16 and 18.

| | |
|---|---|
| From substrates 15, 16 and 18 respectively, (crude material from enzymatic phosphorylation of example 5) ca. | 10.0 mg |
| compound 19 (adenosinetriphosphate, disodium salt) | 22.6 mg |
| NMN-AT: (32 U/ml) | 4.8 µl (0.153 U) |

(According to the instant disclosure, NMN-AT may comprise recombinant nicotinamide mononucleotide-adenylyltransferase (NMN-AT) from *Homo sapiens* (SwissProt ID: Q9HAN9). Alternatively, e.g., NMN-AT from *E. coli* (SwissProt ID: P0A752) or *B. subtilis* (SwissProt ID: P54455) expressed heterologously in *E. coli* may be used.)

Working Procedure:

ATP disodium salt (22.6 mg) and NMN-AT (4.8 µl, 0.153 U) were added to the filtered solution obtained from the enzymatic phosphorylation reaction which included the mononucleotide (compound 15 or an analogue thereof, e.g. compounds 16 and 18). The reaction mixture was incubated for 18 hrs. at 37° C. After warming to 80° C., the mixture was filtered and investigated using HPLC and LC/MS.

In all three experiments, the complete consumption of the mononucleotide (compounds 15, 16 or 18) and the formation of a new compound could be detected by HPLC.

The correct mass of compound 20 was found by mass spectometry (MS: ESI: M$^-$=659.77).

Example 7

One Pot Procedure for Conversion of 3-Carbamoyl-1-((1R,2S,3R,4R)-2,3-dihydroxy-4-hydroxymethyl-cyclopentyl)-pyridinium salt to carba-nicotinamide 1 g (2.16 mmol) of 3-Carbamoyl-1-((1R,2S,3R,4R)-2,3-dihydroxy-4-hydroxymethyl-cyclopentyl)-pyridinium; chloride, 0.242 g (0.4 mmol) ATP di sodium salt, 300 mg Mg Cl2×6H2O (1.45 mmol) 16 U ribosyl kinase, 1.45 g (4.43 mmol) creatinphosphate and 4.27 kU creatine kinase were dissolved in 25 ml sterile water. The mixture was incubated at 35° C. overnight. Thereafter, 2.42 g (4 mmol) ATP di-sodium salt, 440 mg MgCl2×6H2O (2.16 mmol) and 32 U NMNAT were added. The mixture was again incubated at 35° C. overnight and then heated to 90° C. for 5 min, cooled then filtered. Purification was performed by using ion exchange chromatography as described in WO 2007/012494.

Example 8

Conversion of 3-Carbamoyl-1-((1R,2S,3R,4R)-2,3-dihydroxy-4-hydroxymethyl-cyclopentyl)-pyridinium salt to carba-nicotinamide in the Presence of the Enantiomer 3-Carbamoyl-1-(1S,2R,3S,4S))-2,3-dihydroxy-4-hydroxymethyl-cyclopentyl)-pyridinium salt 1 g (2.16 mmol) of a 1:1 mixture consisting of 3-Carbamoyl-1-((1R,2S,3R,4R)-2,3-dihydroxy-4-hydroxymethyl-cyclopentyl)-pyridinium; chloride and 3-Carbamoyl-1-((1S, 2R,3S,4S)-2,3-dihydroxy-4-hydroxymethyl-cyclopentyl)-pyridinium; chloride 0.242 g (0.4 mmol), ATP di sodium salt, 300 mg MgCl2×6H2O (1.45 mmol) 16 U ribosyl kinase, 1.45 g (4.43 mmol) creatinphosphate and 4.27 kU creatine kinase were dissolved in 25 ml sterile water. The mixture was incubated at 35° C. overnight. The reaction was monitored by reversed phase HPLC analysis (ODS Hypersil, 5 µm, 250×4.6 mm Thermo Scientific, Part-Nr.:30105-254630, eluent A=0.1 M triethylammoniumacetate pH 7.0, eluent B=0.2 L 0.1 M triethylammmoniumacetate. pH 7.0+0.8 L acetonitrile, gradient 2 min 0% B, in 23 min 100% B, flow: 1 ml/min, detection: UV/260 nm) which showed that both enantiomers were phosphorylated. The peak corresponding to 3-Carbamoyl-1-((1R,2S,3R,4R)-2,3-dihydroxy-4-hydroxymethyl-cyclopentyl)-pyridinium; chloride and the (1S,2R,3S,4S) enantiomer at 2.96 min disappeared and a new peak corresponding to the phosphorylated products at 3.45 min appeared.

Thereafter 2.42 g (4 mmol) ATP di sodium salt, 440 mg MgCl$_2$×6H$_2$O (2.16 mmol) and 32 U NMN-AT were added. The mixture was incubated at 35° C. overnight. Thereafter, it was heated to 90° C. for 5 mins., cooled then filtered. Reverse phase HPLC analysis showed a peak at 7.92 mins. corresponding to cNAD. At 3.45 mins. a peak remains which corresponds to the phosphorylated (1S,2R,3S,4S) enantiomer. After adding alkaline phosphatase the peak at 7.92 min. is not influenced whereas the peak of the phosphorylated (1S,2R,3S,4S) enantiomer at 3.45 min disappears and a peak at 2.96 mins. appears which corresponds to the 3-Carbamoyl-1-((1S,2R,3S,4S)-2,3-dihydroxy-4-hydroxymethyl-cyclopentyl)-pyridinium salt. Thus cNAD (based on the 1R,2S,3R,4R enantiomer) is not affected, whereas the remaining phosphorylated (1S,2R,3S,4S) enantiomer is de-phosphorylated by alkaline phosphatase.

As a control, the same experiment was performed using only 3-Carbamoyl-1-((1S,2R,3S,4S)-2,3-dihydroxy-4-hydroxymethyl-cyclopentyl)-pyridinium; chloride. The reaction was monitored by HPLC. A peak at 3.45 mins. formed (corresponding to the phosphorylated enantiomer) upon the addition of ribosyl kinase but no peak with a retention time at 7.92 mins. was found in the HPLC chromatogram after the addition of NMN-AT.

Therefore, it possible to start the synthesis of cNAD with an enantiomeric mixture of 2,3-Dihydroxy-4-hydroxymethyl-1-aminocyclopentan consisting of (1R,2S,3R,4R and 1S,2R,3S,4S) enantiomers and to obtain, by the method disclosed herein, solely the biologically relevant examination of cNAD.

Example 9

Enzymatic Conversion of Carba-Nicotinamide Mononucleotide (Compound 15) with NMN-AT and N6 Hexylamino ATP

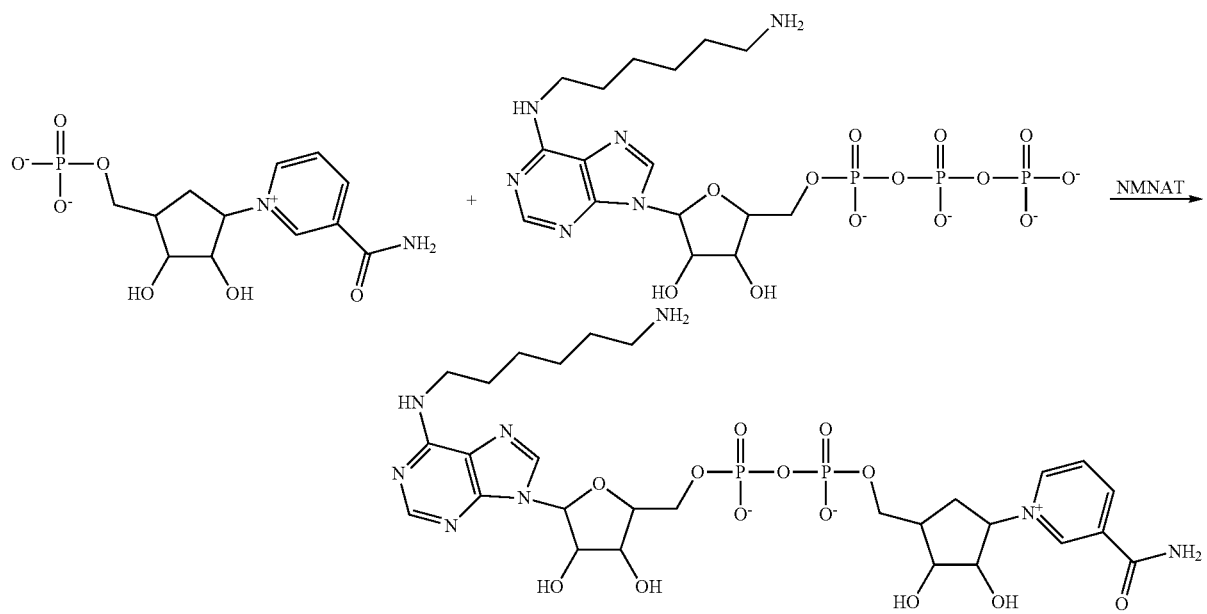

General Working Procedure:

N6-hexylaminoATP disodium salt (0.33 mg, from Jena Bioscience) and nicotinamide mononucleotide adenylyltransferase (NMN-AT, 4.8 µl, 0.153 U) were added to a solution of 1 mg of compound 15. The reaction mixture was incubated for 18 hrs. at 37° C. After warming up to 80° C., the mixture was filtered and investigated by HPLC and LC/MS.

According to the instant example, carba-NMN (compound 15) was completely consumed and a new compound (the corresponding adenosyl derivative) was detected by HPLC. However, embodiments in which carba-NMN is not completely consumed, but only partially consumed prior to a new compound being detected, may be possible within according to the instant disclosure.

The correct mass for the new compound was found (MS: ESI: M$^-$=759.77).

All publications, patents and applications are herein incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for the synthesis of carba-NAD or an analogue thereof, comprising the steps of:

a) phosphorylating a compound of Formula I:

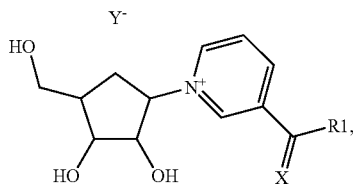

wherein R1 is selected from OH, NH$_2$, O-methyl, N-dimethyl, and methyl, Y$^-$ comprises a counter ion, and X is selected O and S, in a first reaction catalyzed by a nicotinamide-ribosylkinase; and b) adenylating the phosphorylated product of step (a) with a compound of Formula II:

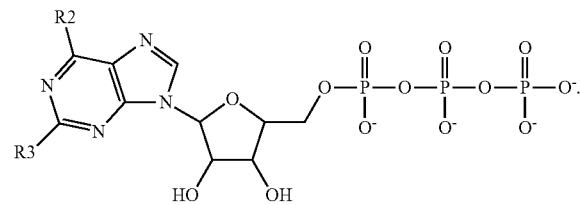

wherein R2 is selected from NH$_2$, OH, and NHalkyl, and R3 is selected from H, OH and NH$_2$, in a second reaction catalyzed by a nicotinamide mononucleotide-adenylyltransferase.

2. The method of claim 1, further comprising the step of recovering a compound of Formula III:

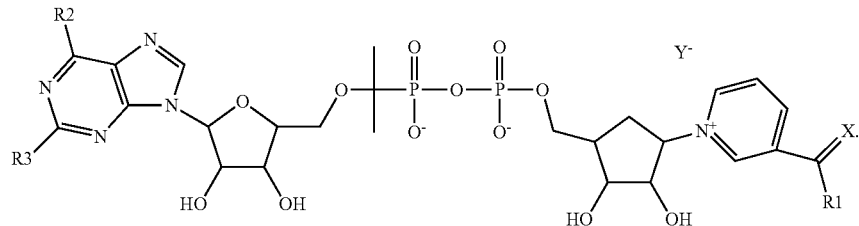

3. The method of claim 1, wherein said nicotinamide-ribosylkinase is found in at least one organism selected from *Saccharomyces cerevisiae, Pseudomonas aeruginosa, Streptococcus sanguinius* and *Homo sapiens*.

4. The method according to claim 1, wherein the nicotinamide-ribosylkinase is heterologously expressed NRK1 native to *Homo sapiens*.

5. The method according to claim 1, wherein the nicotinamide-ribosylkinase is heterologously expressed nadR native to *Streptococcus sanguinius*.

6. The method of claim 1, wherein said nicotinamide mononucleotide-adenylyltransferase is at least one nicotinamide mononucleotide adenylyltransferase found in at least one organism selected from *Bacillus subtilis, Escherichia coli, Methanococcus janashii, Sulfolobus solfataricus, Saccharomyces cerevisiae* and *Homo sapiens*.

7. The method of claim 1, wherein the nicotinamide mononucleotide-adenylyltransferase is heterologously expressed nicotinamide mononucleotide-adenylyltransferase native to *Homo sapiens*.

8. The method of claim 1, wherein the nicotinamide mononucleotide-adenylyltransferase is heterologously expressed nicotinamide mononucleotide adenylyltransferase native to *Escherichia coli*.

9. The method of claim 1, wherein R1 of Formula I is selected from OH, NH$_2$ and O-methyl.

10. The method of claim 1, wherein R2 of Formula II comprises one of NH$_2$ and OH.

11. The method of claim 1, wherein R3 of Formula II comprises one of H or OH.

12. The method of claim 1, wherein X of Formula I comprises O.

13. The method of claim 1, wherein R1 is NH$_2$, R2 is NH$_2$, R3 is H and X is O.

14. The method of claim 1, wherein the compound of Formula I is a mixture of enantiomers.

15. The method of claim 14, wherein the compound of Formula III comprises the cNAD 1R,2S,3R,4R enantiomer of carbamoyl-2-(2,3-dihydroxyl-4-hydroxylmethyl-cyclopentyl)-pyridinium.

16. A method for the synthesis of carba-NAD or an analogue thereof, comprising the steps of:

a) phosphorylating a compound of Formula I:

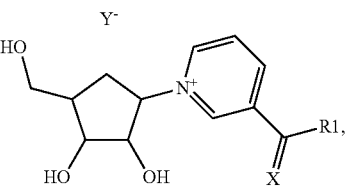

wherein R1 comprises one of OH, NH$_2$, O-methyl, N-dimethyl, and methyl; Y$^-$ comprises a counter ion; and X comprises one of O and S, in a first reaction catalyzed by a nicotinamide-ribosylkinase, wherein said nicotinamide-ribosyl kinase is native to a least one organism selected from *Streptococcus sanguinius* and *Homo sapiens*;

b) adenylating the phosphorylated product of step (a) with a compound of Formula II:

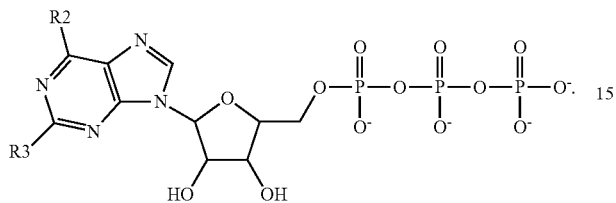

wherein R2 comprises one of NH$_2$, OH, and NHalkyl, and R3 comprises one of H, OH or NH$_2$ in a second reaction catalyzed by at least one nicotinamide mononucleotide-adenylyltransferase selected from *Saccharomyces cerevisiae* and *Homo sapiens*, wherein the second reaction predominately forms a biologically active carba-NAD.

17. The method of claim 16, wherein said NMN-AT is recombinantly generated in at least one organism selected from *E. coli* and *B. subtilis*.

18. The method of claim 16 wherein R1 is selected from OH, NH$_2$ and O-methyl and wherein X is O.

19. The method of claim 16, wherein R1 is NH$_2$, R2 is NH$_2$, R3 is H, and X is O.

20. A method of synthesizing a compound of Formula III, comprising the steps of: adenylating a compound according to Formula B:

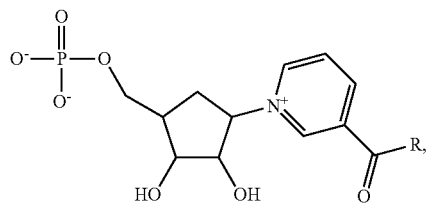

wherein R is selected from NH$_2$, OMe, NMe$_2$, with a least one compound of Formula II:

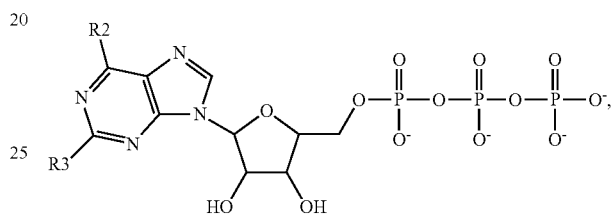

wherein R$_2$ is selected from NH$_2$, OH, and NHalkyl, and R$_3$ is selected from H, OH and NH$_2$, in a reaction catalyzed by a nicotinamide mononucleotide-adenylyltransferase, thereby forming compound of Formula III:

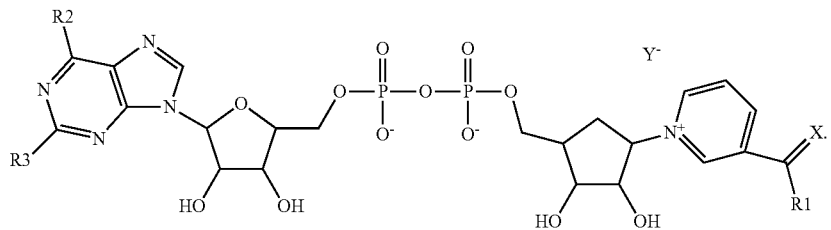

21. The method according to claim 20, wherein the compound according to Formula III is the cNAD 1R,2S,3R,4R enantiomer of carbamoyl-2-(2,3-dihydroxyl-4-hydroxylmethyl-cyclopentyl)-pyridinium.

* * * * *

UNITED STATES PATENT AND TRADEMARK OFFICE
CERTIFICATE OF CORRECTION

PATENT NO. : 8,580,949 B2  
APPLICATION NO. : 13/358146  
DATED : November 12, 2013  
INVENTOR(S) : Duefel et al.

Page 1 of 1

It is certified that error appears in the above-identified patent and that said Letters Patent is hereby corrected as shown below:

In the Claim

Claim 20, Column 18, Line 29 should read as follows:

wherein R2 is selected from NH2, OH, and NHalkyl, and R3 is

Signed and Sealed this
Twenty-fourth Day of December, 2013

Margaret A. Focarino
*Commissioner for Patents of the United States Patent and Trademark Office*